(12) United States Patent
Kalkbrenner et al.

(10) Patent No.: US 9,322,780 B2
(45) Date of Patent: Apr. 26, 2016

(54) WAVELENGTH-RESOLVING AND HIGH SPATIAL RESOLUTION FLUORESCENCE MICROSCOPY

(71) Applicant: Carl Zeiss Microscopy GmbH, Jena (DE)

(72) Inventors: Thomas Kalkbrenner, Jena (DE); Ralf Wolleschensky, Jena (DE)

(73) Assignee: Carl Zeiss Microscopy GmbH, Jena (DE)

(*) Notice: Subject to any disclaimer, the term of this patent is extended or adjusted under 35 U.S.C. 154(b) by 371 days.

(21) Appl. No.: 13/774,539

(22) Filed: Feb. 22, 2013

(65) Prior Publication Data

US 2013/0228704 A1    Sep. 5, 2013

(30) Foreign Application Priority Data

Feb. 22, 2012 (DE) .......................... 10 2012 202 730

(51) Int. Cl.
*G01N 21/64* (2006.01)
*G02B 21/16* (2006.01)
(Continued)

(52) U.S. Cl.
CPC .............. *G01N 21/64* (2013.01); *G01J 3/1804* (2013.01); *G01J 3/4406* (2013.01); *G01N 21/6456* (2013.01); *G02B 21/16* (2013.01)

(58) Field of Classification Search
CPC ...... G01J 3/1804; G01J 3/4406; G02B 21/16; G02B 21/64; G02B 21/6456
USPC .............................................. 250/362, 459.1
See application file for complete search history.

(56) References Cited

U.S. PATENT DOCUMENTS

2002/0167665 A1* 11/2002 Yeung et al. .................. 356/344
2003/0207461 A1* 11/2003 Bell et al. ...................... 436/172
2007/0035818 A1* 2/2007 Bahatt et al. .................. 359/366
(Continued)

FOREIGN PATENT DOCUMENTS

DE 10 2009 060 490 A1 6/2011
WO WO 2012/039636 A2 3/2012

OTHER PUBLICATIONS

Van de Linde et al., "Photoswitching microscopy with standard fluorophores", Appl. Phys B., vol. 93, 2008, pp. 725-731, <doi:10.1007/s00340-008-3250-9>.
(Continued)

*Primary Examiner* — David Porta
*Assistant Examiner* — Carolyn Igyarto
(74) *Attorney, Agent, or Firm* — Patterson Thuente Pedersen, P.A.

(57) ABSTRACT

A method for wavelength-resolving and high spatial resolution fluorescence microscopy in which fluorescence labels in a sample are repeatedly excited to emit fluorescence radiation and frames including images of isolated labels are produced with a microscope. The positions of the images of the isolated fluorescing labels are localized with a localization precision exceeding the optical resolution of the imaging beam path of the microscope. The imaging beam path of the microscope has a diffractive element which, during the imaging, diffracts the image of the sample comprising the isolated fluorescing labels into a first diffraction order so that each frame contains the first diffraction order images of the isolated fluorescing labels. A parameter of the first diffraction order images of the isolated fluorescing labels is evaluated and an indication of the wavelength of the isolated fluorescing labels is derived from this evaluated parameter.

17 Claims, 5 Drawing Sheets

(51) Int. Cl.
*G01J 3/18* (2006.01)
*G01J 3/44* (2006.01)

(56) References Cited

U.S. PATENT DOCUMENTS

| | | |
|---|---|---|
| 2009/0059360 A1 | 3/2009 | Evans et al. |
| 2011/0102787 A1 | 5/2011 | Hess et al. |
| 2011/0160083 A1 | 6/2011 | Hell et al. |
| 2011/0174986 A1 | 7/2011 | Kempe et al. |
| 2012/0224034 A1 | 9/2012 | Kalkbrenner et al. |

OTHER PUBLICATIONS

Webb et al., "Chromatically Resolved Optical Microscope (CROMoscope): A Grating-Based Instrument for Spectral Imaging", Anal. Chem., vol. 81, 2009, pp. 7309-7313, <doi: 10.1021/ac9011655>.

* cited by examiner

Prior Art

WAVELENGTH-RESOLVING AND HIGH SPATIAL RESOLUTION FLUORESCENCE MICROSCOPY

RELATED APPLICATIONS

This application claims the benefit of priority to German Patent Application No. 102012202730.0 filed on Feb. 22, 2012. Said application is hereby fully incorporated by reference herein.

FIELD OF THE INVENTION

The invention relates to a method for wavelength-resolving and high spatial resolution fluorescence microscopy, wherein in a sample fluorescence labels are repeatedly excited to emit fluorescence radiation and frames of the sample are produced with a microscope having an imaging beam path with an optical resolution, wherein the fluorescence labels are excited to emit fluorescence radiation such that at least some of the fluorescence labels are isolated in each frame, the positions of such isolated fluorescence labels are localized in the produced frames with a localization precision exceeding the optical resolution and a high-resolution image of the sample is produced.

The invention further relates to a fluorescence microscope for wavelength-resolving imaging of a sample with a spatial resolution increased compared with an optical resolution, which has an illumination device which is adapted to repeatedly excite fluorescence labels to emit fluorescence radiation in the sample, an imaging device comprising an imaging beam path with the optical resolution, which is adapted to produce frames of the sample with the optical resolution, a control device which is adapted to control the illumination device and the imaging device such that several frames of the sample are produced, wherein the fluorescence labels are excited to emit fluorescence radiation such that at least some of the fluorescence labels are isolated in each frame, the control device is adapted to localize the positions of such isolated fluorescence labels with a localization precision exceeding the optical resolution in the produced frames and to produce a high-resolution image of the sample.

BACKGROUND OF THE INVENTION

Various methods of breaking Abbe's diffraction limit in microscopy have been developed in the state of the art. The term "high resolution" used in this specification addresses a resolution beyond Abbe's diffraction limit. A method abbreviated to PALM (photo activated light microscopy) is known from WO 2006/127692 and DE 102006021317 A1, which uses labels for imaging a sample which labels can be activated e.g. by means of optical radiation. WO 2006/127692 and DE 102006021317 A1, and respective counterparts U.S. Pat. No. 7,626,703 B2 and U.S Patent Publication No. 2011/0160083 A1 are hereby fully incorporated herein by reference. The labels can emit specific fluorescence radiation only in the activated state. Non-activated labels emit no, or at least no noticeable, fluorescence radiation even after irradiation by excitation radiation. The activation radiation is therefore generally called a switching signal. In the PALM method, the switching signal is applied such that at least a certain proportion of activated labels are spaced apart from neighbouring activated labels such that these labels are separated, as measured by the optical resolution of the microscopy, or can be separated subsequently by image processing methods. It is said that at least some of the fluorescence labels are isolated.

After recording the fluorescence radiation, for these isolated emitters the centre of their diffraction-limited images is identified. From this, the position of the labels in the sample can be determined computationally with higher precision than the optical resolution itself allows. This procedure is called localization. The increased resolution by computational determination of the centre of the diffraction-limited images achieves a so called "superresolution". It requires at least some of the activated labels to be distinguishable with the optical resolution, i.e. these activated labels are isolated in the sample. Then their position can be determined with higher precision and they are localized.

To isolate individual labels, the PALM principle utilizes statistical effects. In the case of a label which can be excited to fluorescence radiation only after receiving the switching signal of given intensity, one can ensure, by adjusting the intensity of the switching signal, that the probability of activating labels present in a given unit area of the sample is so small that there are enough domains in which only labels emit fluorescence radiation which are distinguishable with the optical resolution.

The PALM principle was refined with respect to the activation of the labels to be recorded. Thus for example, in the case of labels that have a long-lived non-fluorescing and a short-lived fluorescing state, a separate activation with activation radiation differing spectrally from the excitation radiation is not necessary. Instead the labels of or in the sample are first activated with high-intensity illumination radiation such that the vast majority of the labels is converted to the non-fluorescence-capable long-lived state (e.g. a triplet state). The remaining, still fluorescing labels are thereby isolated in terms of the optical resolution.

It may also be noted that the PALM principle has meanwhile also acquired other abbreviations, such as for example STORM, in the technical literature. In this description, the abbreviation PALM is used for all microscopy techniques which achieve a spatial resolution beyond the optical resolution of the apparatus used by first isolating and then localizing fluorescent molecules. The PALM method has the advantage that no particular high spatial resolution is required for illumination. A simple widefield illumination suffices for activation and/or excitation.

The PALM method uses a sample comprising fluorescent substances. The fluorescent molecules (either all or at least a sub-set of all molecules) are first isolated in terms of the optical resolution of the imaging of the sample and then localized to determine the localization of the molecules with a resolution beyond the diffraction limit of the optical imaging. This methodology can be worked with as soon as the sample has certain fluorescence properties, as explained above. These properties can be achieved by providing the sample with staining material or dies etc. Biological samples can be provided with respective fluorescence material by e.g. transfection. Of course, it is also possible to use a sample which already comes with the respective fluorescence molecules without need to prepare the sample. The term "label" used in this specification shall cover all these options, in particular it shall cover embodiments where a sample preparation step is performed to provide the sample with respective fluorescent molecules and embodiments where the sample already comprises such fluorescent molecules.

The PALM principle requires many frames of the sample to be recorded, each of which contains labels being isolated. In order to image the sample completely, all frames together should ensure that if possible all labels were at least once isolated. As each frame contains a sub-set of the labels—some of these (but not necessarily all) are isolated, the PALM method usually requires a large number of frames, which means that it takes a certain period of time to record a complete image. This is associated with a considerable computational outlay as a large number of labels must be computationally localized in each frame. Large amounts of data are accumulated.

There is now a need not only to record high-resolution images in a colour channel, but to obtain colour information, i.e. an indication of the wavelength of the fluorescing emitters. In fluorescence microscopy, the state of the art knows a microscope according to FIG. 8. The fluorescence microscope 100 shown there comprises an illumination beam path 3 as well as an imaging beam path 4 which illuminate a sample 2 with excitation radiation via a common objective 5 and image the fluorescing sample 2. The illumination beam path 3 is combined with the imaging beam path 4 via a beam splitter 6, usually dichroic in design, such that both illumination radiation from the illumination beam path 3 is incident on the sample 2 through the objective 5 and the imaging of the sample is carried out through the objective 5 and via the imaging beam path 4. The illumination beam path 3 usually has several spectral channels; in the representation in FIG. 8 two laser sources L1 and L2 are shown by way of example, the radiation of which is merged via a beam splitter 5. The illumination beam path 3 thus illuminates the sample 2 with radiation of at least two wavelengths, with the result that a multicolour fluorescence excitation of the sample 2 is effected. The sample 2 also emits multicoloured fluorescence radiation (naturally this could also be the case for a monochrome fluorescence excitation and different fluorescence molecules which fluoresce at different wavelengths). In the imaging beam path 4, the image of the sample 2 is therefore divided into e.g. three colour channels, i.e. directed to three cameras K1, K2 and K3, via two beam splitters 7 and 8 as well as suitable lens systems not described in more detail. The split by the beam splitters 8 and 9 effects a spectrally selective division towards the cameras K1 to K3. Alternatively or in addition, suitable colour filters can also be used. Several colour channels are thus obtained, one for each camera. However, a disadvantage of this design is that the camera systems used are very expensive due to the high diffraction-limited resolution required. Furthermore, the installation space for the microscope 100 is large on account of the required beam paths and colour splitters. Usually, the cameras must be cooled and likewise require a large installation space. A further problem is that the cameras K1, K2 and K3 must be aligned precisely relative to one another so that the images of the individual colour channels are aligned correctly relative to one another. Any alignment error between the beam paths of the individual colour channels would result in a colour aberration generating a chromatic aberration in the image of the sample.

Figure 8:
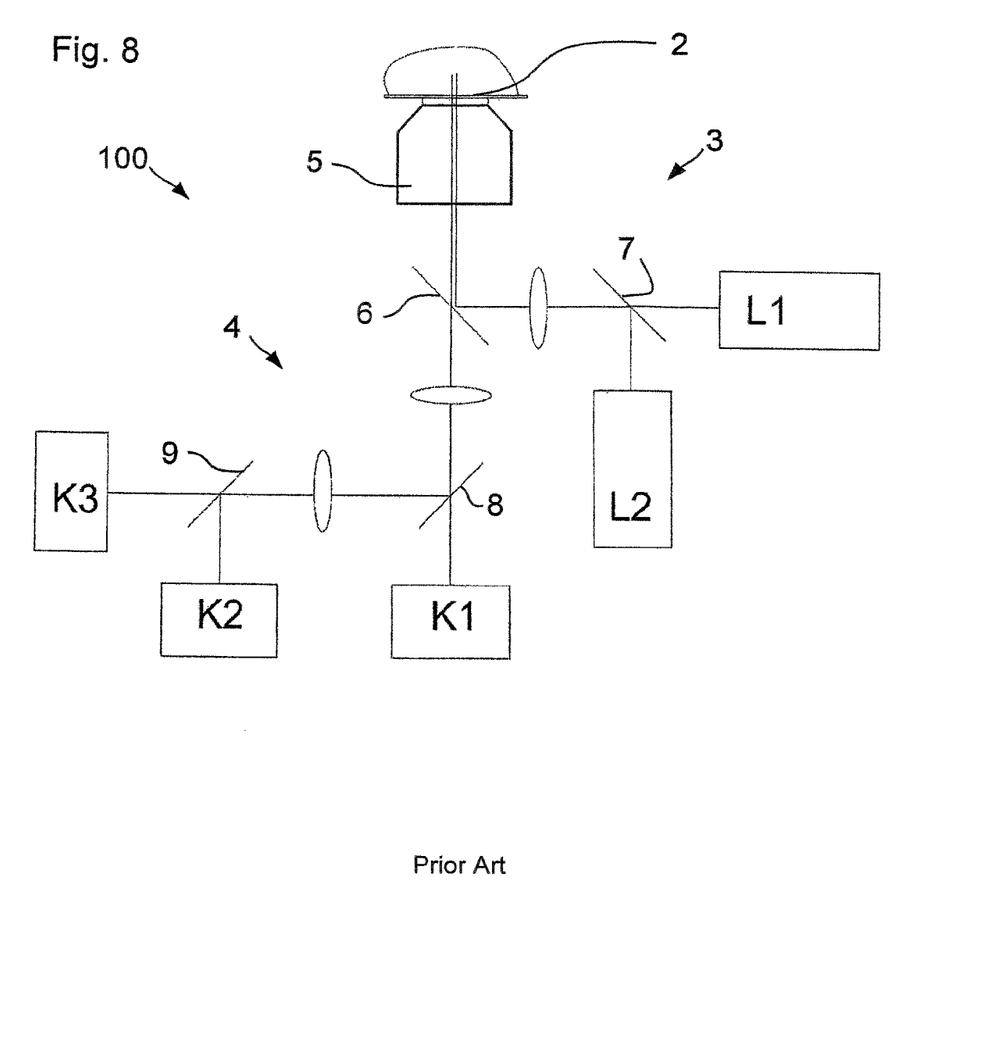
FIG. 8 is a schematic representation of a prior art fluorescence microscope.

One could use the microscope 100 of FIG. 8 for the PALM principle, but then the amount of data accumulating as well as the computational outlay would be multiplied by the number of colour channels.

SUMMARY OF THE INVENTION

An object of embodiments of the invention is therefore to provide a microscope as well as a method for wavelength-resolving, high-resolution fluorescence microscopy which avoids the described disadvantages of the state of the art. In particular, size and range of parts, alignment outlay and amount of data are to be reduced.

This object is achieved according to embodiments of the invention by a method for wavelength-resolving and high spatial resolution fluorescence microscopy, wherein
  a) in a sample fluorescence labels are repeatedly excited to emit fluorescence radiation and frames of the sample, which frames comprise images of the excited and fluorescing labels of the sample, are produced by utilizing a microscope having an imaging beam path with an optical resolution and imaging the sample onto a detector, wherein the labels are excited such that images of at least some of the labels are isolated in each frame in terms of the optical resolution,
  b) in the produced frames the positions of the images of the isolated fluorescence labels are localized with a localization precision exceeding the optical resolution and a high-resolution image of the sample is produced,
  c) the imaging beam path of the microscope comprises a spectrally selective element of pre-defined diffraction properties, which, during the imaging, diffracts the image of the sample comprising the isolated fluorescing labels into a first diffraction order, with the result that each frame contains the first diffraction order images of the isolated fluorescing labels,
  d) in the frames a parameter of the first diffraction order images of the isolated fluorescing labels is evaluated and an indication of the wavelength of the isolated fluorescing labels is derived.

The object is further achieved by a fluorescence microscope for resolving imaging of a sample with a spatial resolution being better than an optical resolution of the microscope, which microscope comprises:
  an illumination device which is designed to repeatedly excite in the sample fluorescence labels to emit fluorescence radiation,
  an imaging device, comprising an imaging beam path and a detector, which imaging device is designed to image the sample with the optical resolution onto the detector and thus produce frames,
  a control device which is adapted to control the illumination device and the imaging device such that several frames of the sample are produced, wherein the labels are excited to emit fluorescence radiation such that at least some of the labels are isolated in each frame in terms of the optical resolution, wherein
  the control device is adapted to localize the positions of the isolated fluorescing labels with a localization precision exceeding the optical resolution in the produced frames and to produce a high-resolution image of the sample,
  the imaging beam path of the microscope has a spectrally selective element of pre-defined diffraction properties, which element, during the imaging, diffracts the image of the sample comprising the isolated fluorescing labels into a first diffraction order, with the result that each frame contains first diffraction order images of the isolated fluorescing labels,
  the control device is designed to evaluate in the frames the first diffraction order images of the isolated fluorescing labels and to derive therefrom an indication of the wavelength of the isolated fluorescing labels.

Embodiments of the invention overcome the limitations of standard multicolour widefield detection for PALM-based high resolution microscopy by using the diffractive element which generates diffraction images of the fluorescence emitters onto the detector. Whereas, with conventional widefield microscopy, such diffraction is to be strictly avoided (it would deteriorate the overall resolution) and colour channels are imaged onto different detectors or separate detector areas, embodiments of the invention image the fluorescing sample such that the sample image on the detector contains a first diffraction order images. The corresponding colour parameter of the isolated labels is obtained from the first diffraction order images. The parameter utilized is preferably selected from a group consisting of: location and distortion of the first diffraction order images.

The evaluation of this parameter is carried out by considering the diffraction properties of the diffractive element. Location and/or distortion of the first diffraction order images can thereby be used to generate a wavelength indication for each isolated label. Different approaches are possible in order to detect both the location and the colour of an given isolated label.

To allocate the detected colour to the detected location, a first variant uses labels which each comprise an ensemble in form of a pair of emitters. A first emitter is paired with a second emitter. In all pairs, the second emitter has the same spectral imaging properties regarding the diffraction effected by the diffractive element. Each first emitter is selected from an emitter group. The members of the emitter group have known but individual spectral fluorescence behaviour (called "chromaticity" below) and bind to sample different molecules or structures. Each emitter pair always consists of the same type of second emitter and one first emitter from the emitter group, i.e. the pairs may differ regarding their first emitter. The first emitters colour different sample molecules or structures differently.

In one embodiment an optical switch that is as bright as possible, i.e. photoefficient, for example a so-called quantum dot, is used for the second emitter. The pair of coupled emitters labels the molecules or structures in the sample by binding the first emitter with the sample structures. As the sample is labelled with the coupled emitter pairs, in each frame the location indication is derived from the position of the second emitter which has the known diffraction behaviour.

The concept of using emitter pairs for the labels can most easily be understood in an example using the letter A, B, C and D for possible types of first fluoresce emitters. The letter Z may designate the type of the second emitter. It is always of the same type in all possible pairs. The labels, thus, comprise the following pairs: AZ, BZ, CZ, and DZ. The first emitter binds to structures in the sample. Which of the first emitters actually binds to a structure depends on the type of the first emitter (A, B, C, D) and of the structure. The term "first emitter" shall emphasize that it is actually this emitter which binds the sample structure or molecules. If one looks at a special position in the sample, it depends on the structure which is present there whether actually a first emitter A, a first emitter B, a first emitter C or a first emitter D is linked to that structure. Although the sample is provided with the labels, all emitter pairs, i.e. AZ, BZ, CZ, DZ are distributed over the sample. Since in all labels the second emitter type Z is present and since further the spectral properties of this second emitter type is known, the diffraction which radiation coming from this emitter type undergoes during imaging is well known. The images recorded for the second emitters allow to identify the location of all emitter pairs. The spectral properties of the emitters A, B, C, D are known. However, one does not know at a given position in the sample which type of first emitter actually is linked to sample structure at that position, as the sample structure is not known at this position, obviously. Evaluating the spectral properties of the first emitters gives a colour information and thus allows structure identification, i.e. one knows whether the sample comprises at a given position a structure binding to a first emitter type A, a first emitter type B, a first emitter type C or a first emitter type D.

The first emitter type in the emitter pair effects the colour labelling. Depending on the type of an actual first emitter in a given pair, radiation from this first emitter is imaged onto the detector at a location according to the first emitter type's emission wavelength due to the effect of the diffractive element. First and second emitters emit independently of each other, i.e. FRET pairs are not involved.

In order to distinguish the chromaticity of the first emitter of a pair, two options exist, which can also be combined to increase accuracy:

1. In the image, the distance of the location of the first emitter from the location of its paired second emitter can be detected. As the spectral influence on the position of the second emitter in the image, i.e. the wavelength behaviour of the second emitter is known, the distance encodes the chromaticity of the first emitter as an absolute measure. The distance can be positive and negative, depending on whether the first emitter of a given pair fluoresces at a shorter or longer wavelength than the associated second emitter of this pair. The image of the first emitter, due to the known effect of the diffractive element is offset in a known spatial direction vis-à-vis the image of the second emitter; shift length and direction distinguish the chromaticities. The shift length corresponds to half the spectral difference.
2. The image of the first emitter, due to the diffraction effect of the diffractive element, is distorted rotationally asymmetrically differently as the image of the second emitter, because the diffractive element causes a colour aberration, which blurs the point spread function of the imaging system. Alternatively or in addition to the evaluation of the distance, it is therefore possible to evaluate the rotational asymmetry of the images which asymmetry is wavelength-dependent. The greater the wavelength difference between first and second emitters, the more rotationally asymmetric the image of the first emitter is. The degree of rotational asymmetry encodes the colour of the actual first emitter.

The options 1 and 2 are particularly simple to realize when the diffractive element is a component which diffracts the majority of the incident radiation into the first diffraction order. Such a component may be for example a blazed grating or a so-called diffractive optical element DOE. A high image quality is obtained when this component is designed such that the image of the second emitter is as unblurred as possible in the first diffraction order. With a blazed grating, the emission wavelength of this second emitter is chosen as blaze wavelength. Radiation from the second emitter is de facto efficiently retro-reflected, then. If such a grating is tilted about its non-diffracting axis (so-called off-axis Littrow configuration), the desired imaging is obtained with which the second emitters, by means of which the location information is obtained, are imaged as unblurred as possible even in the first diffraction order.

At the end of a PALM measurement, most fluorescence labels have been illuminated at least once. In variants nos. 1 and 2 the colour allocation can be carried out after the whole data set was processed by seeking emitter pairs having pre-defined distances in a pre-defined direction and/or having a pre-defined rotational asymmetry. The allocation can be improved still further by using in a targeted manner fluorescence emitters with different emission bandwidths for the first emitter.

The image allocation of first and second emitters can be further simplified and erroneous image allocations can be minimized in that the second emitter type and the first emitter types are chosen such that they show different photon statistics or in that they are influenced such to show different photon statistics. The latter can be carried out by adjusting the excitation power and/or the chemical environment, as is known for example from the publication van de Linde et al., Appl. Physics, B93, page 725, 2008. If the photon statistic of the second emitters differs from that of the first emitters, it is easier to identify the second emitters for each pair. For example, the second emitters can be chosen to be as bright as possible or be such that the photons yield from the second emitters occurs within only one to two camera frames, whereas the emission of the first emitters is accordingly slower and spread over more frames.

Naturally, instead of an emitter pair, a larger ensemble e.g. of three (called "trio" below) or more emitters can also be used, wherein in each ensemble there is always a second emitter which has the properties described above with respect to the emitter pair.

A third option utilizes a single emitter instead of an emitter ensemble, which single emitter likewise comes from a group of emitters having known but different chromaticities, can also be used in a third variant also for localization, i.e. to produce the location indication. Then, the zero and the first diffraction order of the diffractive element are imaged simultaneously onto the detector. This generates an image in the zero and in the first order for each fluorescence emitter. The distances between these two images encode the chromaticity, i.e. colour, the location of the zero order encodes the location information. Here too, alternatively or in addition to the distance, a rotational asymmetry, i.e. the blurring of the first diffraction order image, can be used to determine the chromaticity.

The methods and apparatus according to all option of the invention have the general advantage that no adjustment of colour channels relative to one another is required, as the imaging is carried out with one single detector. Laborious subsequent adjustments of several detectors throughout the life of a microscope are not necessary, too.

Furthermore, the data traffic is significantly reduced as, despite multicolour measurements, only one camera need be read and only the data of one camera processed and stored.

There is greater flexibility in respect of the labels that can be used. Ultimately, the limit here is imposed only by the spectral resolution of the system. This is advantageous in particular when tracking different molecules if the latter are to be tracked simultaneously.

As only one camera is required, the construction outlay, and thus also not least the cost factor, falls as high-resolution cameras are one of the most elaborate and thus most expensive elements of a PALM system.

In the PALM system, the sample is usually marked with the labels. Usually the labels are linked to structures of the sample. The linking should be as close as possible (preferably with a distance around or even below 22 nm in length). However, in the embodiment using emitter ensembles as labels this requirement is relevant only for the second emitter as it is its image which provides the location information. On the other hand, the first emitters, the diffraction images of which provide the colour information, might be connected to the second emitter at comparatively larger distances, provided these distances do not change to a great extent, i.e. are constant (then the determination of the colour information could possibly be difficult).

In the third option, the diffraction images are used in the zero diffraction order for localization, i.e. to obtain the location indication, and in the first diffraction order for colour detection. Thus, the effective photon yield is increased, as each photon is evaluated both for location information and for colour information. As a result, the localization precision increases. However, the diffraction properties in the imaging beam path, which are produced by the diffractive element, must be known precisely. It is advantageous here to carry out a calibration measurement by means of calibrated coloured labels.

It is understood that the features mentioned above and those yet to be explained below can be used, not only in the stated combinations, but also in other combinations or alone, without departing from the scope of the present invention.

BRIEF DESCRIPTION OF THE DRAWINGS

The embodiments of the present invention may be more completely understood in consideration of the following detailed description of various embodiments in connection with the accompanying drawings, in which.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention.

DETAILED DESCRIPTION OF THE DRAWINGS

Figure 1:
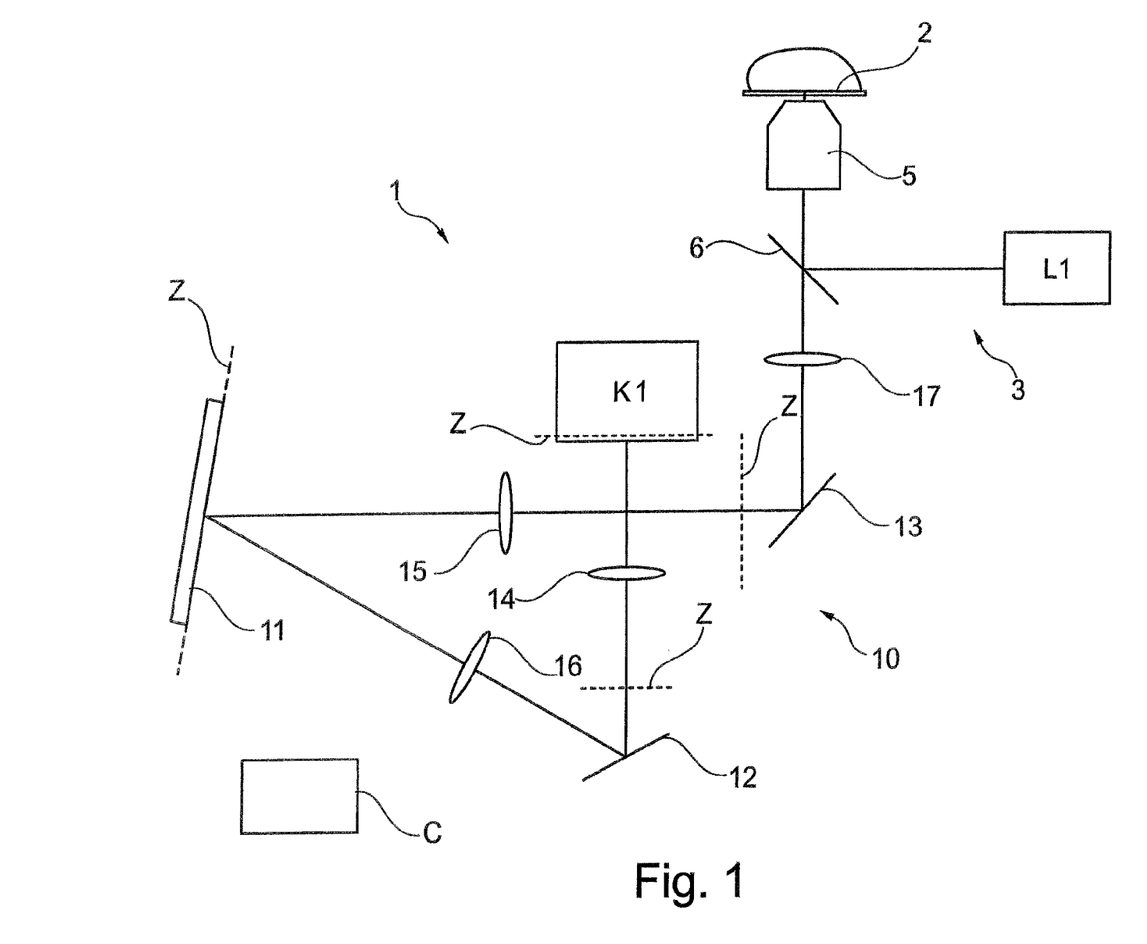
FIG. 1 is a schematic representation of a microscope for carrying out the PALM principle with simultaneous colour resolution.

FIG. 1 schematically shows a fluorescence microscope 1 the operation of which is controlled by a control device C. It is connected to the elements of the microscope 1 via connections that are not shown, in particular to the laser source(s) and the camera. Elements or components which correspond functionally and/or structurally to elements or components which have already been explained with reference to the microscope 100 of FIG. 8, i.e. elements which correspond to the state of the art in respect of their function or structure, are provided with the same reference numbers in FIG. 1. Their description therefore need not be repeated. The camera is an example for a detector.

The microscope 1 of FIG. 1 comprises, in addition to the illumination beam path 3, an imaging beam path 10 which, as will be explained later, works without spectral division into several colour channels. Therefore, only a single camera K1 is required. The imaging of the sample 2 is guided through a diffractive element 11.

The PALM method described above, consisting of an isolating step and a localizing step, is carried out with the microscope. The references named in this respect above, WO 2006/127692 and DE 102006021317 A1, and respective counterparts U.S. Pat. No. 7,626,703 B2 and U.S Patent Publication No. 2011/0160083 A1, are all hereby fully incorporated into this description by reference.

The diffractive element effects that labels fluorescing in different colours in the sample are imaged to different locations on the camera with the location depending on the colour, i.e. wavelength.

The diffractive element 11 may be a blazed grating. It has a so called blaze wavelength at which radiation is efficiently retro-reflected. This grating is tilted about its non-diffracting axis (so-called off-axis Littrow configuration), with the result that radiation at the blaze wavelength is imaged unmodified and in the first diffraction order onto the camera K1. In order that this happens efficiently, both the element 11 and the camera K are arranged in an intermediate image plane Z of the imaging beam path 10. The intermediate image planes Z are provided by lens systems 14 to 16. Reflecting mirrors 12 and 13 keep the beam path compact. The number of the intermediate image planes and the folding are optional. Furthermore, the imaging beam path 10 has a tube lens 17, as known for fluorescence microscopes.

In order to obtain the allocation of the colour to the detected locations of a label in PALM microscopy, a first option uses labels which are each formed by an emitter pair. There a first emitter of a first emitter type is coupled to a second emitter which has known spectral behaviour.

The sample 2 is labelled with emitter pairs, wherein the type of the first emitter in each pair can vary, but each emitter pair has the same type of second emitter. In other words, for all labels, the second emitter is of an identical type. The first emitter comes from an emitter group. It is not known what colour a first emitter in a given emitter pair has. Only the possible colours of the first emitters are known. Thus the colour or chromaticity of a first emitter must be determined for each pair. This colour differs over the sample as the types of first emitters bind differently to different sample structure.

Figure 2:
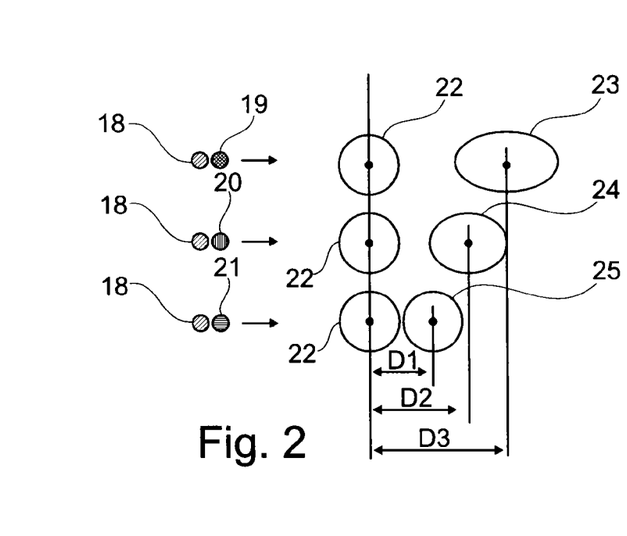
FIG. 2 is a schematic representation relating to a diffraction image which forms in the microscope of FIG. 1 according to a first embodiment option.

The diffractive element 11 in the form of the grating has the effect that, for each isolated label, images in the first diffraction order, i.e. both of the second emitter and of the differently-coloured first emitter types, are imaged on the camera K. This is illustrated schematically in FIG. 2. In FIG. 2, different labels are shown, each consisting of a second emitter 18 and a first emitter 19 to 21, wherein the first emitters differ in respect of their chromaticity and their binding characteristics. In the diffraction image on the camera K, there appears for a label a diffraction image 22 of the second emitter 18 and a diffraction image 23, displaced thereto by a distance D3, in this case of the first emitter 19. The distance D3 is given by half the spectral difference of the fluorescence radiation from the second emitter 18 and from the first emitter 19.

Below the images of the emitter pair 18, 19 FIG. 2 shows the images of an emitter pair 18, 20 the first emitter 20 of which fluoresces at a wavelength different from that of the first emitter 19 of the pair shown above in FIG. 2. Accordingly, a diffraction image 24 of the first emitter 20 is obtained which lies at a different distance D2 from the diffraction image 22 of the pair's second emitter 18.

There is yet another distance, namely D1, for a diffraction image 25 when the pair comprises a first emitter 21 of a third chromaticity.

Figure 3:
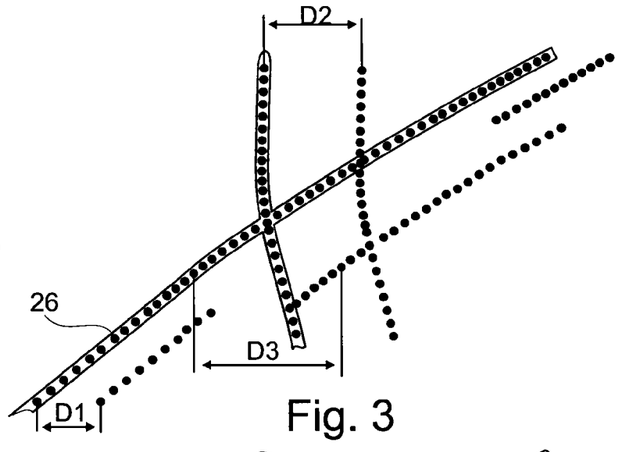
FIG. 3 is a schematic representation of a sample imaging after determination of location information and before the allocation of colour information.
Figure 4:
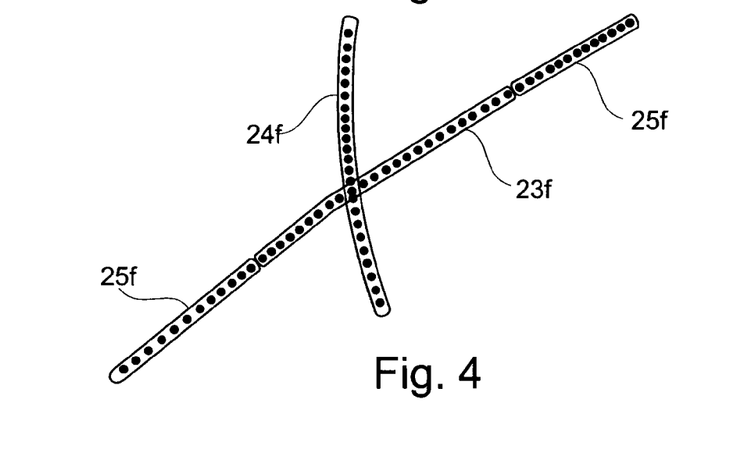
FIG. 4 is a representation similar to FIG. 3, but after the allocation of the colour information.

As the colour properties of the first emitters 19, 20, 21 are known, but it is not known what chromaticity the first emitter in a given emitter pair has, an image such as is shown by way of example in FIG. 3 is obtained on the camera K after localization according to PALM. Continuous sample structures 26 are identified by using the images of the second emitters 18. The images of the first emitters 19 to 21 lie at a distance which depends on their colour. As it is only necessary to distinguish between known states (chromaticities), in this case the three distances D1, D2 and D3 (the number of chromaticities, i.e. of first emitter types can naturally be larger), the gap each diffraction image 22 has to the associated diffraction image of the first emitter can easily be determined. The distance or gap encodes the chromaticity and thus the wavelength, with the result that after proper processing, the structures can be allocated the colours 23f, 24f and 25f in FIG. 4, wherein the reference numbers refer to the corresponding chromaticities of the first emitters 23 to 25.

Figure 5:
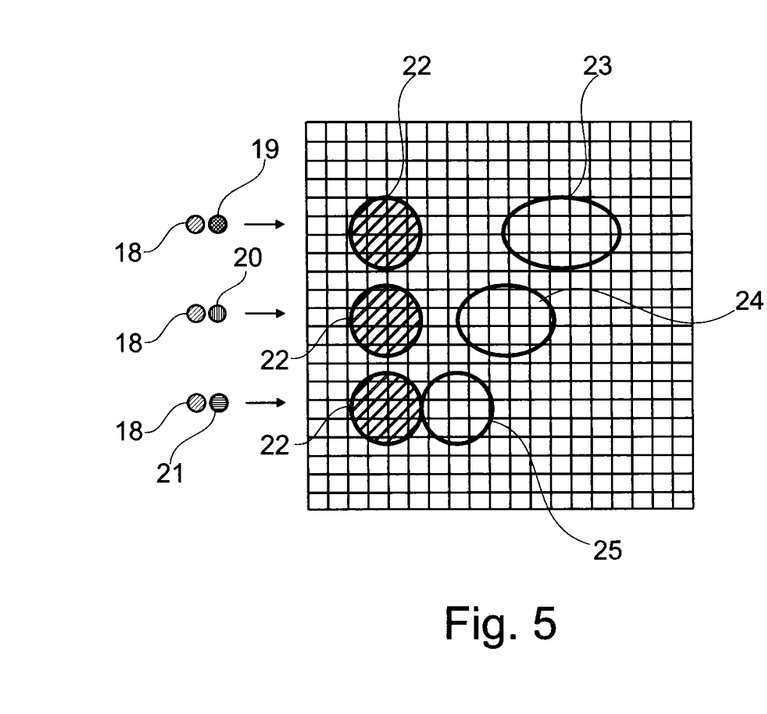
FIG. 5 is a schematic representation similar to FIG. 2 to determine the colour information according to a second embodiment option.

FIG. 5 shows a second option of how the images produced with the microscope 1 of FIG. 5 can be evaluated when using the described fluorescence emitter pairs. Here, it is not the distance between the diffraction images that is evaluated, but the distortion of the diffraction images 23 to 25 of the second emitters 19 to 21 codes chromaticity and thus colour of the first emitters.

Figure 6:
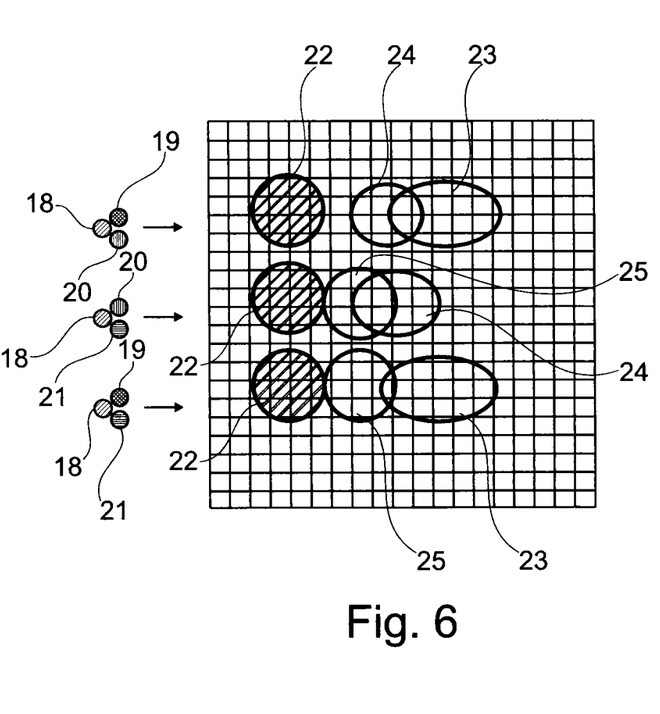
FIG. 6 is a representation similar to FIG. 5 for a combination of the first with the second option.

FIG. 6 shows a situation in which the number of the different possible labels is further increased by using trios, i.e. labels which each consist of the second emitter 18 and two different of the first emitter types, e.g. 19+20 or 20+21 or 19+21. Accordingly, for each diffraction image, in addition to the diffraction image 22 of the second emitter 18, a combination of two further diffraction images is obtained, namely the diffraction images 23+24, or 24+25, or 23+25. If this trio is combined with the conventional pairs according to FIG. 5, then, using three different fluorescence emitters only one of which is common in all pairs, six different labels exist.

Naturally, it is possible to combine the first and the second option, i.e. the evaluation of the distance, thus of the spectral difference between diffraction image 22 and the diffraction image of the first emitters 19 to 21, and the evaluation of rotational asymmetry, e.g. the blurring of the diffraction images of the first fluorescence emitters, are used. This increases the precision of distinction in sample sections in which the sections do not allow a clear resolution because the luminous fluorescence emitters are too close together.

A modification of the microscope of FIG. 1 consists of using a customary conventional grating instead of the blazed grating or a DOE as diffractive element 11. This is particular suitable for a third option which labels the sample with labels comprising only one single emitter (i.e. no emitter ensembles). The label comes from a group of emitters each having a known (but individual) colour.

Figure 7:
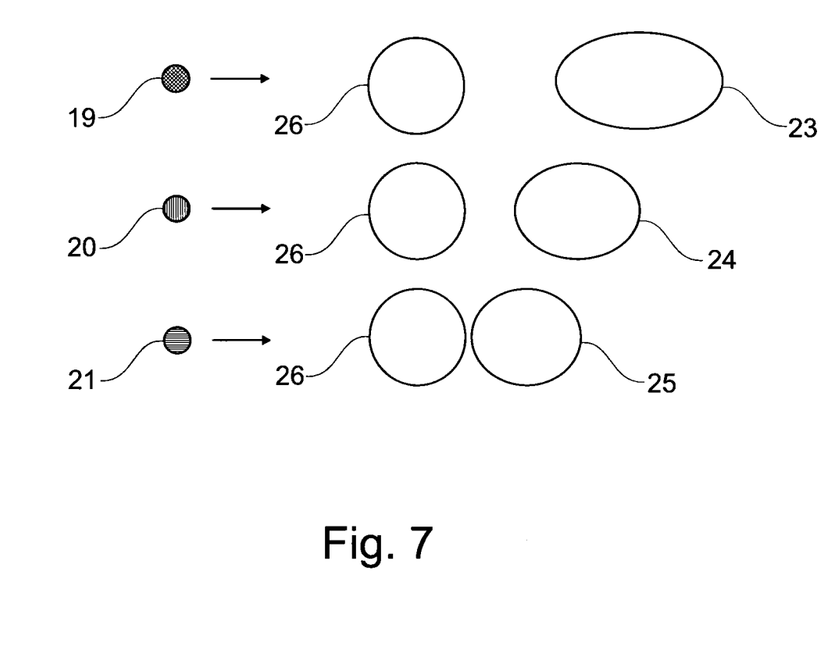
FIG. 7 is a representation similar to FIG. 2 for a third embodiment option for wavelength-resolving and high spatial resolution fluorescence microscopy.

In this case, the imaging beam path 10 is designed such that the zero and the first diffraction order of the grating are imaged simultaneously onto the camera K. Thus, there is obtained for each label 19 to 21 a respective first diffraction image 23 to 25 as well as in addition an undiffracted image (zero diffraction order) 26. The first diffraction order carries the colour information, either through its distance from the image 26 of the zero diffraction order, or through its blurring. The evaluation is carried out analogously to the first or second option.

The foregoing descriptions present numerous specific details that provide a thorough understanding of various embodiments of the invention. It will be apparent to one skilled in the art that various embodiments, having been disclosed herein, may be practiced without some or all of these specific details. In other instances, components as are known to those of ordinary skill in the art have not been described in detail herein in order to avoid unnecessarily obscuring the present invention. It is to be understood that even though numerous characteristics and advantages of various embodiments are set forth in the foregoing description, together with details of the structure and function of various embodiments, this disclosure is illustrative only. Other embodiments may be constructed that nevertheless employ the principles and spirit of the present invention. Accordingly, this application is intended to cover any adaptations or variations of the invention.

For purposes of interpreting the claims for the present invention, it is expressly intended that the provisions of 35 U.S.C. §112(f) are not to be invoked unless the specific terms "means for" or "step for" are recited in a claim.

The invention claimed is:

1. A method for wavelength-resolving and high spatial resolution fluorescence microscopy, comprising:
   using an illumination device to repeatedly excite fluorescence labels in a sample to emit fluorescence radiation;
   producing a plurality of frames of the sample and a high-resolution image of the sample using a microscope having a detector and an imaging beam path, the imaging beam path having an optical resolution and a spectrally selective diffractive element with known diffraction properties, the frames comprising images of excited and fluorescing labels of the sample imaged onto the detector, wherein the labels are excited such that images of at least some of the fluorescence labels are isolated in each frame and the positions of the images of the isolated fluorescing labels are localized in the frames with a localization precision exceeding the optical resolution, and wherein the diffractive element of the imaging beam path diffracts the image of the sample comprising the isolated fluorescing labels into a first diffraction order such that each frame contains the first diffraction order images of the isolated fluorescing labels;
   evaluating at least one parameter of the first diffraction order images of the isolated fluorescing labels in the frames;
   deriving an indication of the wavelength of the isolated fluorescing labels from the evaluated parameter; and
   wherein the labels comprise emitter ensembles wherein each emitter ensemble is formed by at least one first emitter and a second emitter, wherein in all of the emitter ensembles the second emitter is of the same type and has known spectral emission properties and the first emitter is selected from a group of emitters, with each member of the group of emitters having known spectral emission properties, wherein the members of the group differ in their spectral emission properties and in their capability to mark sample structure, whereby the image of each isolated fluorescing label in the frames consists of a diffraction image of the at least one first emitter and, separated therefrom, a diffraction image of the second emitter, and wherein the positions of the isolated fluorescing labels in the sample are determined from the position of the diffraction images of the second emitters, and the at least one parameter comprises the distance between the diffraction images of the second emitter and the associated at least one first emitter.

2. The method according to claim 1, wherein the image of each isolated fluorescing label is imaged into a zero diffraction order onto the detector and the position of each isolated fluorescing label is determined from the zero order diffracted image.

3. The method according to claim 1, wherein the ensembles are pairs.

4. The method according to claim 1, wherein the diffractive element diffracts the majority of incident radiation into a first diffraction order, and wherein the diffractive element is a blazed grating or a diffractive optical element (DOE).

5. The method according to claim 1, wherein the diffraction causes a non-rotationally symmetric blurring of the images of the isolated fluorescing labels and a value of the non-rotationally symmetric blurring is the evaluated parameter.

6. The method according to claim 5, wherein the at least one parameter further comprises a rotational asymmetry of the images of the first emitters.

7. The method according to claim 6, wherein the ensembles are pairs.

8. The method according to claim 6, wherein the diffractive element diffracts the majority of incident radiation into a first diffraction order, and wherein the diffractive element is a blazed grating or a diffractive optical element (DOE).

9. The method according to claim 5, wherein for each image of an isolated fluorescing label, the location indication is corrected for a diffraction-limited offset by using the determined wavelength indication of the label and by taking into account the known diffraction properties of the spectrally selective diffractive element.

10. The method according to claim 1, wherein the image of each isolated fluorescing label is imaged into a zero diffraction order onto the detector and a distance between the zero diffraction order image and the first diffraction order image of this label is the evaluated parameter.

11. The method according to claim 10, wherein the image of each isolated fluorescing label is imaged into a zero diffraction order onto the detector and the position of each isolated fluorescing label is determined from the zero order diffracted image.

12. A fluorescence microscope for wavelength-resolving imaging of a sample with a spatial resolution being better than an optical resolution of the microscope, the microscope comprising:
   an illumination device configured to repeatedly excite fluorescence labels in the sample to emit fluorescence radiation;
   an imaging device, comprising an imaging beam path and a detector, configured to image the sample onto the detector with the optical resolution, so as to produce a plurality of frames in which at least some of the labels excited by the illumination device are isolated in each frame, the imaging beam path including a spectrally selective diffractive element with known diffraction properties configured to diffract the image of the sample comprising the isolated fluorescing labels into a first diffraction order such that each frame contains first diffraction order images of the isolated fluorescing labels; and
   a control device configured to control the illumination device and the imaging device, such that the positions of the isolated fluorescing labels are localized with a localization precision exceeding the optical resolution in the frames, and so as to produce a high-resolution image of the sample, and wherein the control device is configured to evaluate, in the frames, the first diffraction order images of the isolated fluorescing labels and derive therefrom an indication of the wavelength of the isolated fluorescing labels; and
   wherein the fluorescence labels in the sample comprise emitter ensembles wherein each ensemble is formed by at least one first emitter and a second emitter, wherein in all the emitter ensembles the second emitter is of the same type and has known spectral emission properties and the first emitter is selected from a group of emitters, with each member of the group of emitters having known spectral emission properties, wherein the members of the group differ in their spectral emission properties and in their capability to mark sample structure, whereby the image of each isolated fluorescing label in the frames consists of a diffraction image of the at least one first emitter and, separated therefrom, a diffraction image of the second emitter, and wherein the control device is configured to determine the positions of the isolated fluorescing labels in the sample from the position of the diffraction images of the second emitters, and evaluate the distance between the diffraction images of the second emitter and the associated at least one first emitter to derive therefrom the indication of the wavelength of the isolated fluorescing labels.

13. The fluorescence microscope according to claim 12, wherein the imaging device is further configured such that the image of each isolated fluorescing label is imaged into a zero diffraction order onto the detector and the control device is configured to determine the position of each isolated fluorescing label from the zero order diffracted image.

14. The fluorescence microscope according to claim 12, wherein the diffractive element is configured to diffract the majority of incident radiation into a first diffraction order, and wherein the diffractive element is a blazed grating or a diffractive optical element (DOE).

15. The fluorescence microscope according to claim 12, wherein the diffraction causes a non-rotationally symmetric blurring of the images of the isolated fluorescing labels and the control device is configured to evaluate a value of the non-rotationally symmetric blurring.

16. The fluorescence microscope according to claim 15, wherein the control device is configured to evaluate a rotational asymmetry of the images of the first emitters to derive therefrom the indication of the wavelength of the isolated fluorescing labels.

17. The fluorescence microscope according to claim 15, wherein for each image of an isolated fluorescing label, the control device is configured to correct the location indication for a diffraction-limited offset by using the determined wavelength indication of the label and by taking into account the known diffraction properties of the spectrally selective diffractive element.

* * * * *